(12) United States Patent
Al-Ali et al.

(10) Patent No.: US 7,729,733 B2
(45) Date of Patent: Jun. 1, 2010

(54) CONFIGURABLE PHYSIOLOGICAL MEASUREMENT SYSTEM

(75) Inventors: Ammar Al-Ali, Tustin, CA (US);
Walter M. Weber, Laguna Hills, CA (US); Joe E. Kiani, Laguna Hills, CA (US)

(73) Assignee: Masimo Laboratories, Inc., Irvine, CA (US)

( * ) Notice: Subject to any disclaimer, the term of this patent is extended or adjusted under 35 U.S.C. 154(b) by 1083 days.

(21) Appl. No.: 11/367,036

(22) Filed: Mar. 1, 2006

(65) Prior Publication Data

US 2006/0211932 A1 Sep. 21, 2006

Related U.S. Application Data

(60) Provisional application No. 60/657,596, filed on Mar. 1, 2005, provisional application No. 60/657,281, filed on Mar. 1, 2005, provisional application No. 60/657,268, filed on Mar. 1, 2005, provisional application No. 60/657,759, filed on Mar. 1, 2005.

(51) Int. Cl.
*A61B 5/145* (2006.01)

(52) U.S. Cl. ...................................... 600/310

(58) Field of Classification Search .................. 600/310, 600/322, 323
See application file for complete search history.

(56) References Cited

U.S. PATENT DOCUMENTS

| 3,998,550 A | 12/1976 | Konishi et al. |
| 4,157,708 A | 6/1979 | Imura |
| 4,167,331 A | 9/1979 | Nielsen |
| 4,266,554 A | 5/1981 | Hamaguri |
| 4,446,871 A | 5/1984 | Imura |
| 4,586,513 A | 5/1986 | Hamaguri |
| 4,621,643 A | 11/1986 | New et al. |
| 4,653,498 A | 3/1987 | New et al. |

(Continued)

FOREIGN PATENT DOCUMENTS

| WO | WO 98/43071 | 10/1998 |

(Continued)

OTHER PUBLICATIONS

Schmitt, Joseph M.; Zhou, Guan-Xiong; Miller, Justin, *Measurement of Blood Hematocrit by Dual-wavelength Near-IR Photoplethysmography*, published May 1992, Proc. SPIE vol. 1641, p. 150-161, Physiological Monitoring and Early Detection Diagnostic Methods, Thomas S. Mang; Ed. (SPIE homepage), in 12 pages.

*Primary Examiner*—Eric F Winakur
*Assistant Examiner*—Etsub D Berhanu
(74) *Attorney, Agent, or Firm*—Knobbe Martens Olson & Bear LLP

(57) ABSTRACT

A physiological measurement system has a sensor, a processor, a communications link and information elements. The sensor is configured to transmit light having a plurality of wavelengths into a tissue site and to generate a sensor signal responsive to the transmitted light after tissue attenuation. The processor is configured to operate on the sensor signal so as to derive at least one physiological parameter. The communications link is adapted to provide communications between the sensor and the processor. The information elements are distributed across at least one of the sensor, the processor and the communications link and provide operational information corresponding to at least one of the sensor, the processor and the communications link.

20 Claims, 5 Drawing Sheets

U.S. PATENT DOCUMENTS

| | | |
|---|---|---|
| 4,685,464 A | 8/1987 | Goldberger |
| 4,694,833 A | 9/1987 | Hamaguri |
| 4,700,708 A | 10/1987 | New et al. |
| 4,714,341 A | 12/1987 | Hamaguri et al. |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,832,484 A | 5/1989 | Aoyagi et al. |
| 4,846,183 A | 7/1989 | Martin |
| 4,863,265 A | 9/1989 | Flower et al. |
| 4,867,571 A | 9/1989 | Frick et al. |
| 4,869,254 A | 9/1989 | Stone et al. |
| 4,907,876 A | 3/1990 | Suzuki et al. |
| 4,911,167 A | 3/1990 | Corenman et al. |
| 4,934,372 A | 6/1990 | Corenman et al. |
| 4,942,877 A | 7/1990 | Sakai et al. |
| 4,955,379 A | 9/1990 | Hall |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,986,665 A | 1/1991 | Yamanishi et al. |
| 4,997,769 A | 3/1991 | Lundsgaard |
| RE33,643 E | 7/1991 | Isaacson et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle et al. |
| 5,069,213 A | 12/1991 | Polczynski |
| 5,078,136 A | 1/1992 | Stone et al. |
| 5,163,438 A | 11/1992 | Gordon et al. |
| 5,190,040 A | 3/1993 | Aoyagi |
| 5,209,230 A | 5/1993 | Swedlow et al. |
| 5,259,381 A | 11/1993 | Cheung et al. |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,331,549 A | 7/1994 | Crawford, Jr. |
| 5,335,659 A | 8/1994 | Pologe et al. |
| 5,337,744 A | 8/1994 | Branigan |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| 5,421,329 A | 6/1995 | Casciani et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| RE35,122 E | 12/1995 | Corenman et al. |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,551,423 A | 9/1996 | Sugiura |
| 5,553,615 A | 9/1996 | Carim et al. |
| 5,555,882 A | 9/1996 | Richardson et al. |
| 5,562,002 A | 10/1996 | Lalin |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,713,355 A | 2/1998 | Richardson et al. |
| D393,830 S | 4/1998 | Tobler et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,800,348 A | 9/1998 | Kaestle et al. |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,010 A | 10/1998 | Hibl |
| 5,818,985 A | 10/1998 | Merchant et al. |
| 5,823,950 A | 10/1998 | Diab et al. |
| 5,823,952 A | 10/1998 | Levinson et al. |
| 5,827,182 A | 10/1998 | Raley et al. |
| 5,830,131 A | 11/1998 | Caro et al. |
| 5,830,137 A | 11/1998 | Sharf |

| Patent | Type | Date | Inventor |
|---|---|---|---|
| 5,833,618 | A | 11/1998 | Caro et al. |
| 5,839,439 | A | 11/1998 | Nierlich et al. |
| RE36,000 | E | 12/1998 | Swedlow et al. |
| 5,842,979 | A | 12/1998 | Jarman |
| 5,851,178 | A | 12/1998 | Aronow |
| 5,851,179 | A | 12/1998 | Ritson et al. |
| 5,853,364 | A | 12/1998 | Baker, Jr. et al. |
| 5,857,462 | A | 1/1999 | Thomas et al. |
| 5,860,919 | A | 1/1999 | Kiani-Azarbayjany et al. |
| 5,865,736 | A | 2/1999 | Baker, Jr. et al. |
| 5,876,348 | A | 3/1999 | Sugo |
| 5,885,213 | A | 3/1999 | Richardson et al. |
| 5,890,929 | A | 4/1999 | Mills et al. |
| 5,891,024 | A | 4/1999 | Jarman et al. |
| 5,904,654 | A | 5/1999 | Wohltmann et al. |
| 5,910,108 | A | 6/1999 | Solenberger |
| 5,916,154 | A | 6/1999 | Hobbs et al. |
| 5,919,133 | A | 7/1999 | Taylor |
| 5,919,134 | A | 7/1999 | Diab |
| 5,921,921 | A | 7/1999 | Potratz et al. |
| 5,934,277 | A | 8/1999 | Mortz |
| 5,934,925 | A | 8/1999 | Tobler et al. |
| 5,940,182 | A | 8/1999 | Lepper, Jr. et al. |
| 5,954,644 | A | 9/1999 | Dettling |
| 5,978,691 | A | 11/1999 | Mills |
| 5,983,122 | A | 11/1999 | Jarman et al. |
| 5,995,855 | A | 11/1999 | Kiani et al. |
| 5,995,856 | A | 11/1999 | Mannheimer et al. |
| 5,995,859 | A | 11/1999 | Takahashi |
| 5,997,343 | A | 12/1999 | Mills et al. |
| 5,999,841 | A | 12/1999 | Aoyagi et al. |
| 6,002,952 | A | 12/1999 | Diab et al. |
| 6,006,119 | A | 12/1999 | Soller et al. |
| 6,011,986 | A | 1/2000 | Diab et al. |
| 6,014,576 | A | 1/2000 | Raley |
| 6,018,673 | A | 1/2000 | Chin et al. |
| 6,018,674 | A | 1/2000 | Aronow |
| 6,023,541 | A | 2/2000 | Merchant et al. |
| 6,027,452 | A | 2/2000 | Flaherty et al. |
| 6,036,642 | A | 3/2000 | Diab et al. |
| 6,045,509 | A | 4/2000 | Caro et al. |
| 6,064,898 | A | 5/2000 | Aldrich |
| 6,067,462 | A | 5/2000 | Diab et al. |
| 6,068,594 | A | 5/2000 | Schloemer et al. |
| 6,073,037 | A | 6/2000 | Alam et al. |
| 6,081,735 | A | 6/2000 | Diab et al. |
| 6,083,172 | A | 7/2000 | Baker, Jr. et al. |
| 6,088,607 | A | 7/2000 | Diab et al. |
| 6,094,592 | A | 7/2000 | Yorkey et al. |
| 6,104,938 | A | 8/2000 | Huiku |
| 6,110,522 | A | 8/2000 | Lepper, Jr. et al. |
| 6,112,107 | A | 8/2000 | Hannula |
| 6,122,042 | A | 9/2000 | Wunderman et al. |
| 6,144,868 | A | 11/2000 | Parker |
| 6,151,516 | A | 11/2000 | Kiani-Azarbayjany et al. |
| 6,151,518 | A | 11/2000 | Hayashi |
| 6,152,754 | A | 11/2000 | Gerhardt et al. |
| 6,154,667 | A | 11/2000 | Miura et al. |
| 6,157,041 | A | 12/2000 | Thomas et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,226,539 | B1 | 5/2001 | Potratz |
| 6,229,856 | B1 | 5/2001 | Diab et al. |
| 6,230,035 | B1 | 5/2001 | Aoyagi et al. |
| 6,236,872 | B1 | 5/2001 | Diab et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,272,363 | B1 | 8/2001 | Casciani et al. |
| 6,278,522 | B1 | 8/2001 | Lepper, Jr. et al. |
| 6,280,213 | B1 | 8/2001 | Tobler et al. |
| 6,285,895 | B1 | 9/2001 | Ristolainen et al. |
| 6,285,896 | B1 | 9/2001 | Tobler et al. |
| 6,298,252 | B1 | 10/2001 | Kovach et al. |
| 6,304,675 | B1 | 10/2001 | Osbourn et al. |
| 6,304,767 | B1 | 10/2001 | Soller et al. |
| 6,321,100 | B1 | 11/2001 | Parker |
| 6,330,468 | B1 | 12/2001 | Scharf |
| 6,334,065 | B1 | 12/2001 | Al-Ali et al. |
| 6,341,257 | B1 | 1/2002 | Haaland |
| 6,343,224 | B1 | 1/2002 | Parker |
| 6,349,228 | B1 | 2/2002 | Kiani et al. |
| 6,351,658 | B1 | 2/2002 | Middleman et al. |
| 6,356,774 | B1 | 3/2002 | Bernstein et al. |
| 6,360,114 | B1 | 3/2002 | Diab et al. |
| 6,363,269 | B1 | 3/2002 | Hanna et al. |
| 6,371,921 | B1 | 4/2002 | Caro et al. |
| 6,374,129 | B1 | 4/2002 | Chin et al. |
| 6,377,828 | B1 | 4/2002 | Chaiken et al. |
| 6,377,829 | B1 | 4/2002 | Al-Ali |
| 6,388,240 | B2 | 5/2002 | Schulz et al. |
| 6,393,310 | B1 | 5/2002 | Kuenstner |
| 6,397,091 | B2 | 5/2002 | Diab et al. |
| 6,397,092 | B1 | 5/2002 | Norris et al. |
| 6,397,093 | B1 | 5/2002 | Aldrich |
| 6,408,198 | B1 | 6/2002 | Hanna et al. |
| 6,411,833 | B1 | 6/2002 | Baker, Jr. et al. |
| 6,415,166 | B1 | 7/2002 | Van Hoy et al. |
| 6,415,233 | B1 | 7/2002 | Haaland |
| 6,415,236 | B2 | 7/2002 | Kobayashi et al. |
| 6,430,525 | B1 | 8/2002 | Weber et al. |
| 6,434,408 | B1 | 8/2002 | Heckel |
| 6,441,388 | B1 | 8/2002 | Thomas et al. |
| 6,453,184 | B1 | 9/2002 | Hyogo et al. |
| 6,463,310 | B1 | 10/2002 | Swedlow et al. |
| 6,463,311 | B1 | 10/2002 | Diab |
| 6,470,199 | B1 | 10/2002 | Kopotic et al. |
| 6,480,729 | B2 | 11/2002 | Stone |
| 6,490,466 | B1 | 12/2002 | Fein et al. |
| 6,497,659 | B1 | 12/2002 | Rafert |
| 6,501,974 | B2 | 12/2002 | Huiku |
| 6,501,975 | B2 | 12/2002 | Diab et al. |
| 6,504,943 | B1 | 1/2003 | Sweatt et al. |
| 6,505,060 | B1 | 1/2003 | Norris |
| 6,505,061 | B1 | 1/2003 | Larson |
| 6,505,133 | B1 | 1/2003 | Hanna |
| 6,510,329 | B2 | 1/2003 | Heckel |
| 6,515,273 | B2 | 2/2003 | Al-Ali |
| 6,519,486 | B1 | 2/2003 | Edgar, Jr. et al. |
| 6,519,487 | B1 | 2/2003 | Parker |
| 6,522,398 | B2 | 2/2003 | Cadell et al. |
| 6,525,386 | B1 | 2/2003 | Mills et al. |
| 6,526,300 | B1 | 2/2003 | Kiani et al. |
| 6,526,301 | B2 | 2/2003 | Larsen et al. |
| 6,528,809 | B1 | 3/2003 | Thomas et al. |
| 6,537,225 | B1 | 3/2003 | Mills |
| 6,541,756 | B2 | 4/2003 | Schulz et al. |
| 6,542,764 | B1 | 4/2003 | Al-Ali et al. |
| 6,546,267 | B1 | 4/2003 | Sugiura |
| 6,553,241 | B2 | 4/2003 | Mannheimer et al. |
| 6,564,077 | B2 | 5/2003 | Mortara |
| 6,571,113 | B1 | 5/2003 | Fein et al. |
| 6,580,086 | B1 | 6/2003 | Schulz et al. |
| 6,582,964 | B1 | 6/2003 | Samsoondar et al. |
| 6,584,336 | B1 | 6/2003 | Ali et al. |
| 6,584,413 | B1 | 6/2003 | Keenan et al. |
| 6,591,123 | B2 | 7/2003 | Fein et al. |
| 6,594,511 | B2 | 7/2003 | Stone et al. |
| 6,595,316 | B2 | 7/2003 | Cybulski et al. |
| 6,597,933 | B2 | 7/2003 | Kiani et al. |
| 6,600,940 | B1 | 7/2003 | Fein et al. |
| 6,606,509 | B2 | 8/2003 | Schmitt |
| 6,606,510 | B2 | 8/2003 | Swedlow et al. |
| 6,606,511 | B1 | 8/2003 | Ali et al. |

| | | | | | | |
|---|---|---|---|---|---|---|
| 6,611,698 | B1 | 8/2003 | Yamashita et al. | 6,816,741 | B2 | 11/2004 | Diab |
| 6,614,521 | B2 | 9/2003 | Samsoondar et al. | 6,819,950 | B2 | 11/2004 | Mills |
| 6,615,064 | B1 | 9/2003 | Aldrich | 6,822,564 | B2 | 11/2004 | Al-Ali |
| 6,615,151 | B1 | 9/2003 | Scecina et al. | 6,825,619 | B2 | 11/2004 | Norris |
| 6,618,602 | B2 | 9/2003 | Levin | 6,826,419 | B2 | 11/2004 | Diab et al. |
| 6,622,095 | B2 | 9/2003 | Kobayashi et al. | 6,829,496 | B2 | 12/2004 | Nagai et al. |
| 6,628,975 | B1 | 9/2003 | Fein et al. | 6,830,711 | B2 | 12/2004 | Mills et al. |
| 6,631,281 | B1 | 10/2003 | Kastle | 6,836,679 | B2 | 12/2004 | Baker, Jr. et al. |
| 6,632,181 | B2 | 10/2003 | Flaherty et al. | 6,839,579 | B1 | 1/2005 | Chin |
| 6,640,116 | B2 | 10/2003 | Diab | 6,839,580 | B2 | 1/2005 | Zonios et al. |
| 6,643,530 | B2 | 11/2003 | Diab et al. | 6,839,582 | B2 | 1/2005 | Heckel |
| 6,650,917 | B2 | 11/2003 | Diab et al. | 6,842,702 | B2 | 1/2005 | Haaland et al. |
| 6,654,623 | B1 | 11/2003 | Kastle | 6,845,256 | B2 | 1/2005 | Chin et al. |
| 6,654,624 | B2 | 11/2003 | Diab et al. | 6,847,835 | B1 | 1/2005 | Yamanishi |
| 6,657,717 | B2 | 12/2003 | Cadell et al. | 6,850,787 | B2 | 2/2005 | Weber et al. |
| 6,658,276 | B2 | 12/2003 | Kianl et al. | 6,850,788 | B2 | 2/2005 | Al-Ali |
| 6,658,277 | B2 | 12/2003 | Wasserman | 6,852,083 | B2 | 2/2005 | Caro et al. |
| 6,661,161 | B1 | 12/2003 | Lanzo et al. | 6,861,639 | B2 | 3/2005 | Al-Ali |
| 6,662,033 | B2 | 12/2003 | Casciani et al. | 6,869,402 | B2 | 3/2005 | Arnold |
| 6,665,551 | B1 | 12/2003 | Suzuki | 6,882,874 | B2 | 4/2005 | Huiku |
| 6,668,183 | B2 | 12/2003 | Hicks et al. | 6,898,452 | B2 | 5/2005 | Al-Ali et al. |
| 6,671,526 | B1 | 12/2003 | Aoyagi et al. | 6,912,049 | B2 | 6/2005 | Pawluczyk et al. |
| 6,671,531 | B2 | 12/2003 | Al-Ali et al. | 6,917,422 | B2 | 7/2005 | Samsoondar et al. |
| 6,675,031 | B1 | 1/2004 | Porges et al. | 6,919,566 | B1 | 7/2005 | Cadell |
| 6,675,106 | B1 | 1/2004 | Keenan et al. | 6,920,345 | B2 | 7/2005 | Al-Ali et al. |
| 6,678,543 | B2 | 1/2004 | Diab et al. | 6,921,367 | B2 | 7/2005 | Mills |
| 6,681,126 | B2 | 1/2004 | Solenberger | 6,922,645 | B2 | 7/2005 | Haaland et al. |
| 6,684,090 | B2 | 1/2004 | Ali et al. | 6,928,311 | B1 | 8/2005 | Pawluczyk et al. |
| 6,684,091 | B2 | 1/2004 | Parker | 6,931,268 | B1 | 8/2005 | Kiani-Azarbayjany et al. |
| 6,687,620 | B2 | 2/2004 | Haaland et al. | 6,931,269 | B2 | 8/2005 | Terry |
| 6,694,157 | B1 | 2/2004 | Stone et al. | 6,934,570 | B2 | 8/2005 | Kiani et al. |
| 6,697,655 | B2 | 2/2004 | Sueppel et al. | 6,939,305 | B2 | 9/2005 | Flaherty et al. |
| 6,697,656 | B1 | 2/2004 | Al-Ali | 6,943,348 | B1 | 9/2005 | Coffin, IV |
| 6,697,658 | B2 | 2/2004 | Al-Ali | 6,944,487 | B2 | 9/2005 | Maynard et al. |
| RE38,476 | E | 3/2004 | Diab et al. | 6,950,687 | B2 | 9/2005 | Al-Ali |
| 6,699,194 | B1 | 3/2004 | Diab et al. | 6,961,598 | B2 | 11/2005 | Diab |
| 6,701,170 | B2 | 3/2004 | Stetson | 6,970,792 | B1 | 11/2005 | Diab |
| 6,708,049 | B1 | 3/2004 | Berson et al. | 6,975,891 | B2 | 12/2005 | Pawluczyk |
| 6,711,503 | B2 | 3/2004 | Haaland | 6,979,812 | B2 | 12/2005 | Al-Ali |
| 6,714,803 | B1 | 3/2004 | Mortz | 6,985,764 | B2 | 1/2006 | Mason et al. |
| 6,714,804 | B2 | 3/2004 | Al-Ali et al. | 6,987,994 | B1 | 1/2006 | Mortz |
| 6,714,805 | B2 | 3/2004 | Jeon et al. | 6,993,371 | B2 | 1/2006 | Kiani et al. |
| RE38,492 | E | 4/2004 | Diab et al. | 6,996,427 | B2 | 2/2006 | Ali et al. |
| 6,719,705 | B2 | 4/2004 | Mills | 6,999,904 | B2 | 2/2006 | Weber et al. |
| 6,720,734 | B2 | 4/2004 | Norris | 7,001,337 | B2 | 2/2006 | Dekker |
| 6,721,584 | B2 | 4/2004 | Baker, Jr. et al. | 7,003,338 | B2 | 2/2006 | Weber et al. |
| 6,721,585 | B1 | 4/2004 | Parker | 7,003,339 | B2 | 2/2006 | Diab et al. |
| 6,725,074 | B1 | 4/2004 | Kastle | 7,006,856 | B2 | 2/2006 | Baker, Jr. et al. |
| 6,725,075 | B2 | 4/2004 | Al-Ali | 7,015,451 | B2 | 3/2006 | Dalke et al. |
| 6,726,634 | B2 | 4/2004 | Freeman | 7,024,233 | B2 | 4/2006 | Al et al. |
| 6,735,459 | B2 | 5/2004 | Parker | 7,027,849 | B2 | 4/2006 | Al-Ali |
| 6,741,875 | B1 | 5/2004 | Pawluczyk et al. | 7,030,749 | B2 | 4/2006 | Al-Ali |
| 6,741,876 | B1 | 5/2004 | Scecina et al. | 7,039,449 | B2 | 5/2006 | Al-Ali |
| 6,743,172 | B1 | 6/2004 | Blike | 7,041,060 | B2 | 5/2006 | Flaherty et al. |
| 6,745,060 | B2 | 6/2004 | Diab et al. | 7,044,918 | B2 | 5/2006 | Diab |
| 6,745,061 | B1 | 6/2004 | Hicks et al. | 2001/0044700 | A1 | 11/2001 | Koboyashi et al. |
| 6,748,253 | B2 | 6/2004 | Norris et al. | 2001/0045532 | A1 | 11/2001 | Schulz et al. |
| 6,748,254 | B2 | 6/2004 | O'Neil et al. | 2002/0021269 | A1 | 2/2002 | Rast |
| 6,754,515 | B1 | 6/2004 | Pologe | 2002/0038078 | A1 | 3/2002 | Ito |
| 6,754,516 | B2 | 6/2004 | Mannheimer | 2002/0038081 | A1 | 3/2002 | Fein et al. |
| 6,760,607 | B2 | 7/2004 | Al-Ali | 2002/0059047 | A1 | 5/2002 | Haaland |
| 6,760,609 | B2 | 7/2004 | Jacques | 2002/0082488 | A1* | 6/2002 | Al-Ali et al. ............... 600/323 |
| 6,770,028 | B1 | 8/2004 | Ali et al. | 2002/0095078 | A1* | 7/2002 | Mannheimer et al. ....... 600/323 |
| 6,771,994 | B2 | 8/2004 | Kiani et al. | 2002/0111748 | A1 | 8/2002 | Kobayashi et al. |
| 6,773,397 | B2 | 8/2004 | Kelly | 2002/0156353 | A1 | 10/2002 | Larson |
| 6,778,923 | B2 | 8/2004 | Norris et al. | 2002/0161291 | A1 | 10/2002 | Kiani et al. |
| 6,780,158 | B2 | 8/2004 | Yarita | 2002/0183819 | A1 | 12/2002 | Struble |
| 6,788,849 | B1 | 9/2004 | Pawluczyk | 2003/0109775 | A1 | 6/2003 | O'Neil et al. |
| 6,792,300 | B1 | 9/2004 | Diab et al. | 2003/0120160 | A1 | 6/2003 | Yarita |
| 6,801,797 | B2 | 10/2004 | Mannheimer et al. | 2003/0139657 | A1 | 7/2003 | Solenberger |
| 6,801,799 | B2 | 10/2004 | Mendelson | 2003/0195402 | A1 | 10/2003 | Fein et al. |
| 6,810,277 | B2 | 10/2004 | Edgar, Jr. et al. | 2004/0006261 | A1 | 1/2004 | Swedlow et al. |
| 6,813,511 | B2 | 11/2004 | Diab et al. | 2004/0033618 | A1 | 2/2004 | Haass et al. |

| | | |
|---|---|---|
| 2004/0059209 A1 | 3/2004 | Al-Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2004/0147823 A1 | 7/2004 | Kiani et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167382 A1 | 8/2004 | Gardner et al. |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0033128 A1 | 2/2005 | Ali et al. |
| 2005/0043902 A1 | 2/2005 | Haaland et al. |
| 2005/0049469 A1 | 3/2005 | Aoyagi et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0228253 A1 | 10/2005 | Debreczeny |
| 2005/0250997 A1 | 11/2005 | Takeda et al. |
| 2006/0030764 A1 | 2/2006 | Porges et al. |

FOREIGN PATENT DOCUMENTS

| | | |
|---|---|---|
| WO | WO 00/59374 | 10/2000 |
| WO | WO 03/068060 | 8/2003 |

* cited by examiner

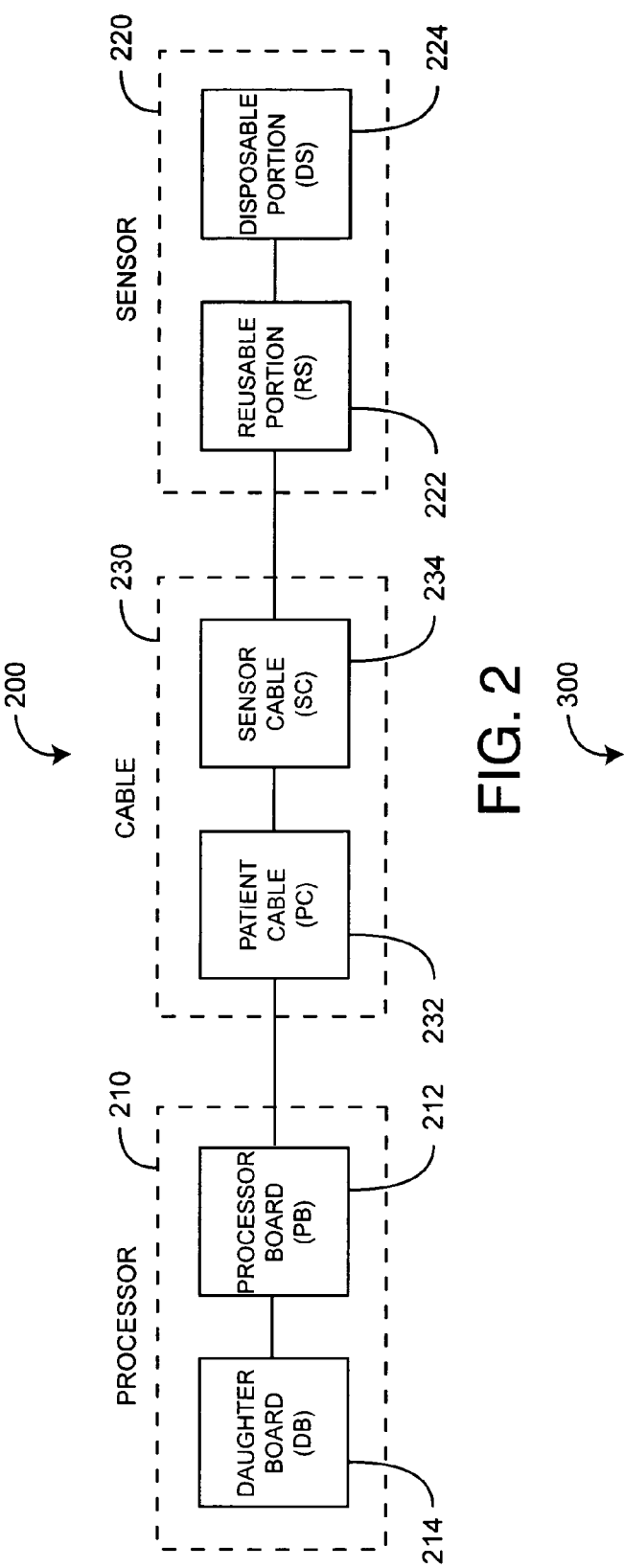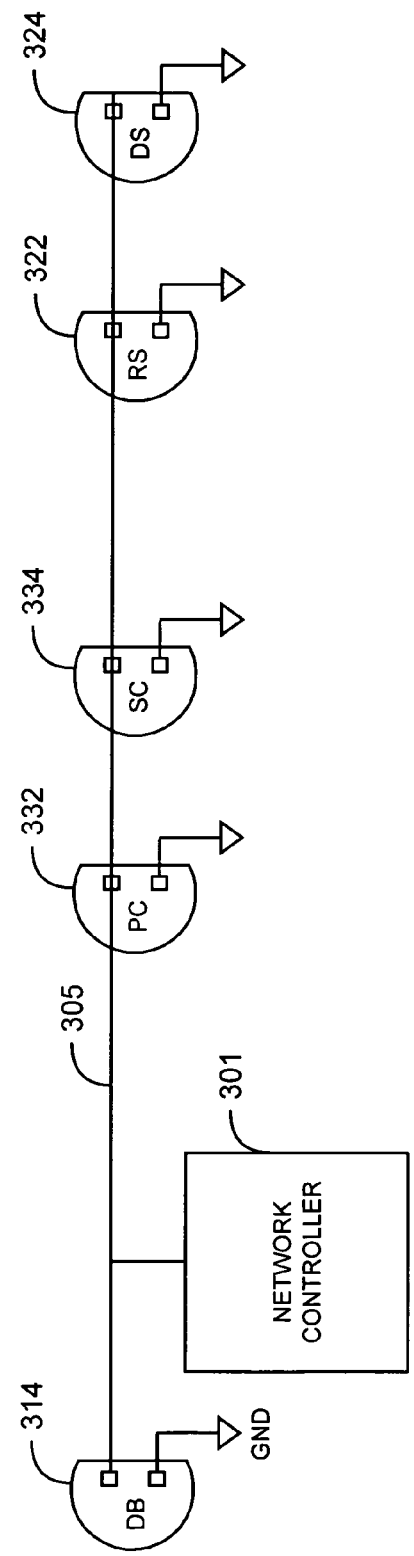

CONFIGURABLE PHYSIOLOGICAL MEASUREMENT SYSTEM

PRIORITY CLAIM TO RELATED PROVISIONAL APPLICATIONS

The present application claims priority benefit under 35 U.S.C. §119(e) to U.S. Provisional Patent Application Ser. No. 60/657,596, filed Mar. 1, 2005, entitled "Multiple Wavelength Sensor," No. 60/657,281, filed Mar. 1, 2005, entitled "Physiological Parameter Confidence Measure," No. 60/657,268, filed Mar. 1, 2005, entitled "Configurable Physiological Measurement System," and No. 60/657,759, filed Mar. 1, 2005, entitled "Noninvasive Multi-Parameter Patient Monitor." The present application incorporates the foregoing disclosures herein by reference.

INCORPORATION BY REFERENCE OF COPENDING RELATED APPLICATIONS

The present application is related to the following copending U.S. utility applications:

| | App. Sr. No. | Filing Date | Title | Atty Dock. |
|---|---|---|---|---|
| 1 | 11/367,013 | Mar. 1, 2006 | Multiple Wavelength Sensor Emitters | MLR.002A |
| 2 | 11/366,995 | Mar. 1, 2006 | Multiple Wavelength Sensor Equalization | MLR.003A |
| 3 | 11/366,209 | Mar. 1, 2006 | Multiple Wavelength Sensor Substrate | MLR.004A |
| 4 | 11/366,210 | Mar. 1, 2006 | Multiple Wavelength Sensor Interconnect | MLR.005A |
| 5 | 11/366,833 | Mar. 1, 2006 | Multiple Wavelength Sensor Attachment | MLR.006A |
| 6 | 11/366,997 | Mar. 1, 2006 | Multiple Wavelength Sensor Drivers | MLR.009A |
| 7 | 11/367,034 | Mar. 1, 2006 | Physiological Parameter Confidence Measure | MLR.010A |
| 8 | 11/367,036 | Mar. 1, 2006 | Configurable Physiological Measurement System | MLR.011A |
| 9 | 11/367,033 | Mar. 1, 2006 | Noninvasive Multi-Parameter Patient Monitor | MLR.012A |
| 10 | 11/367,014 | Mar. 1, 2006 | Noninvasive Multi-Parameter Patient Monitor | MLR.013A |
| 11 | 11/366,208 | Mar. 1, 2006 | Noninvasive Multi-Parameter Patient Monitor | MLR.014A |

The present application incorporates the foregoing disclosures herein by reference.

BACKGROUND OF THE INVENTION

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$, at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \epsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952 5,769,785, and 5,758,644, which are owned by Masimo and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

SUMMARY OF THE INVENTION

A physiological measurement system has a sensor that transmits optical radiation at a multiplicity of wavelengths other than or including the red and infrared wavelengths utilized in pulse oximeters. The system also has a processor that determines the relative concentrations of blood constituents other than or in addition to $HbO_2$ and Hb, such as carboxyhemoglobin (HbCO), methemoglobin (MetHb), fractional oxygen saturation, total hemaglobin (Hbt) and blood glucose to name a few. Further, such a system may be combined with other physiological parameters such as noninvasive blood pressure (NIBP). There is a need to easily configure such a physiological measurement system from compatible components capable of measuring various physiological parameters.

BRIEF DESCRIPTION OF THE DRAWINGS

FIG. 2 is a detailed block diagram of a configurable physiological measurement system embodiment;

FIG. 3 is a detailed block diagram of networked information elements in a configurable physiological measurement system;

DETAILED DESCRIPTION OF THE PREFERRED EMBODIMENTS

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Figure 1:
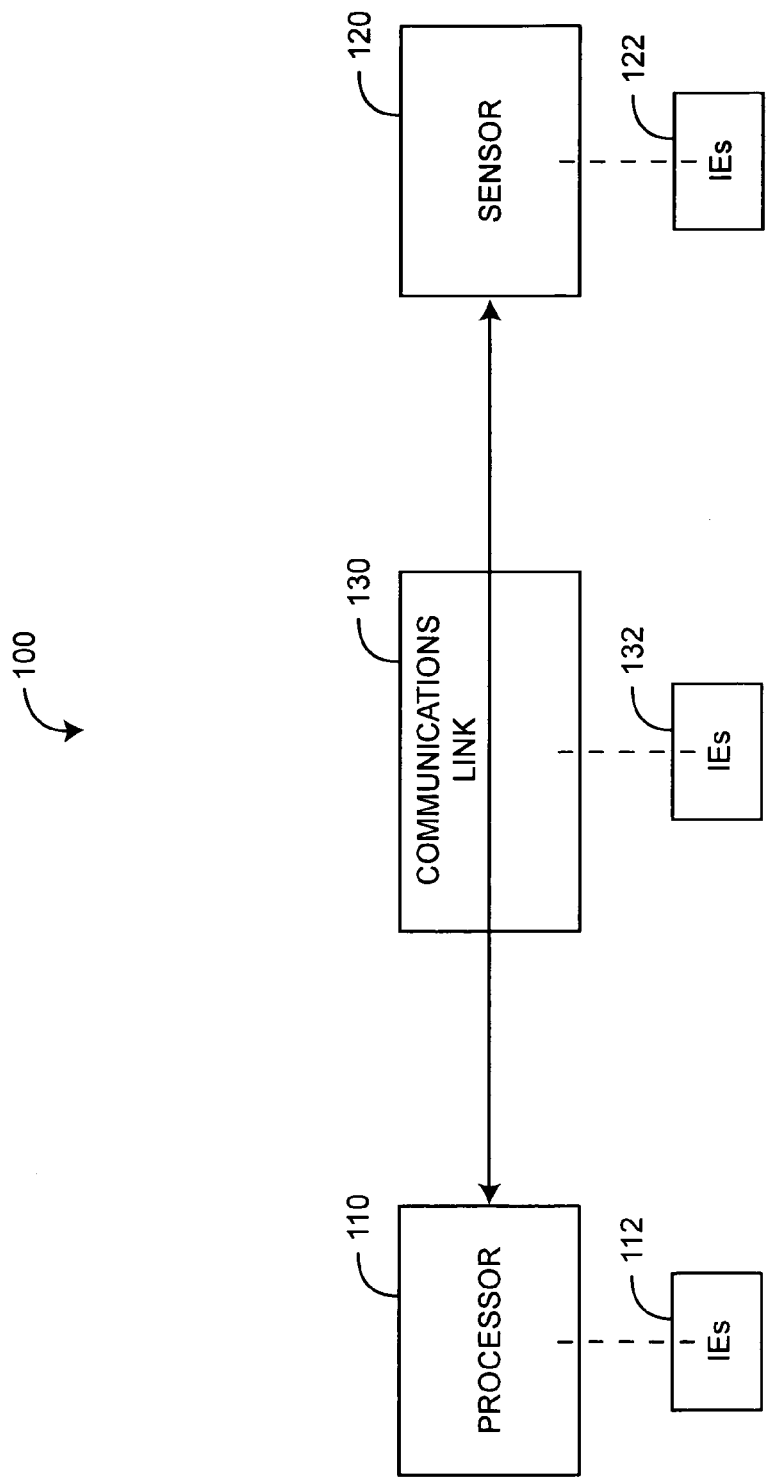
FIG. 1 is a general block diagram of a configurable physiological measurement system.

FIG. 1 illustrates a configurable physiological measurement system 100 having a processor 110, a sensor 120 and a communications link 130. In one embodiment, the sensor 120 has two or more light emitters that transmit optical radiation of two or more wavelengths into a tissue site and at least one detector that generates a signal responsive to the optical radiation after attenuation by the tissue site. Multiple wavelength sensors are described in U.S. patent application Ser. No. 10/719,928, entitled Blood Parameter Measurement System, assigned to Masimo Corporation, Irvine, Calif. and incorporated by reference herein.

The processor 110 generates drive signals so as to activate the sensor emitters and inputs and processes the corresponding detector signal so as determine the relative concentrations of two or more blood constituents. The communications link 130 provides communications between the processor 110 and sensor 120 including transmitting the drive signals from the processor 110 to the sensor 120 and the detector signals from the sensor 120 to the processor 110. In one embodiment, the communications link 130 is a cable and corresponding sensor and processor connectors that provide a wired connection between the processor 110 and connector 120. In another embodiment, the communications link 130 provides a wireless connection between the processor 110 and connector 120. The wireless connection may utilize Bluetooth®, IEEE 802.11 or similar wireless technologies.

As shown in FIG. 1, the configurable physiological measurement system 100 also has information elements 112, 122, 132 distributed across the processor 110, the sensor 120 and the communications link 130, which provide system configuration information, as described below. The information elements 112, 122, 132 may be memory devices, such as described below, or other active or passive electrical components. The information provided by the information elements 112, 122, 132 may be digital data stored in memory or component values determined by DC, AC or combinations of DC and AC voltages or currents. The information element 112, 122, 132 information may be determined by the processor 110 or by a reader or other device in communication with the information elements 112, 122, 132 and the processor 110.

FIG. 2 illustrates configurable physiological measurement system embodiments having processor 210, sensor 220 and cable 230 components. In one embodiment, the processor 210 has a processor printed circuit board "board" 212 and an optional daughter board 214, which plugs into and expands the functionality of the processor board 212. For example, the daughter board 214 may be a noninvasive blood pressure (NIBP) controller that communicates with a blood pressure sensor and the processor board 212 so as to measure blood pressure parameters.

Also shown in FIG. 2, in one embodiment the sensor 220 is a "resposable" sensor comprising a reusable portion 222 and a disposable portion 224. In a particular embodiment, the reusable portion has at least one of a reusable emitter portion and a reusable detector portion, and the disposable portion 224 has at least one of a disposable emitter portion, a disposable detector portion and a disposable tape for attaching the reusable sensor 222 to a tissue site. A resposable sensor is described in U.S. Pat. No. 6,725,075 entitled Resposable Pulse Oximetry Sensor, assigned to Masimo Corporation and incorporated by reference herein.

Further shown in FIG. 2, in one embodiment the cable 230 is a patient cable 232 or a sensor cable 234 or a combination of a patient cable 232 and a sensor cable 234. A sensor cable 234 is fixedly attached at one end to a sensor and has a connector at the other end for attaching to a monitor or a patient cable. A patient cable 234 has connectors at both ends for interconnecting a sensor or sensor cable to a monitor.

FIG. 3 illustrates an information element (IE) network 300 that advantageously enables a physiological measurement system 200 (FIG. 2) to be composed of various components 214-234 (FIG. 2) having, perhaps, differing parameter measurement capabilities, as described above. The IE network 300 also allows various components to "plug and play," i.e. interoperate without hardware or software modification, as described with respect to FIG. 4, below. Further, the IE network 300 provides for forward and backward compatibility between sensors and processors, as described with respect to FIGS. 5A-B, below.

As shown in FIG. 3, the IE network 300 has information elements 314-334, a network controller 301 and a communications path 305. In one embodiment, the network controller 301 resides on or is otherwise incorporated within a processor board 212 (FIG. 2). The information elements 314-334 correspond to the physiological measurement system components 210-230 (FIG. 2). In one embodiment, there may be zero, one, two or more information elements 314-334 on or within each physiological measurement system component 214-224 (FIG. 2). For example, the information elements 314-324 may include a DB element 314 mounted on a daughter board 214 (FIG. 2), a RS element 322 mounted within a reusable sensor portion 222 (FIG. 2), a DS element 324 mounted within a disposable sensor portion 224 (FIG. 2), a PC element 332 mounted within a patient cable 232 (FIG. 2) or connector thereof, and a SC element 334 mounted within a sensor cable 234 (FIG. 2) or connector thereof.

Also shown in FIG. 3, in one embodiment the information elements 314-334 are EPROMs or EEPROMs or a combination of EPROMs or EEPROMs within a particular component 210-230 (FIG. 2). In an advantageous embodiment, the communications path 305 is a single shared wire. This reduces the burden on the components 210-230 (FIG. 2) and associated connectors, which may have a relatively large number of conductors just for drive signals and detector signals when a multiplicity of sensor emitters are utilized for multiple parameter measurements. An information element 314-324 may be, for example, a Dallas Semiconductor DS2506 EPROM available from Maxim Integrated Products, Inc., Sunnyvale, Calif., or equivalent.

Figure 4:
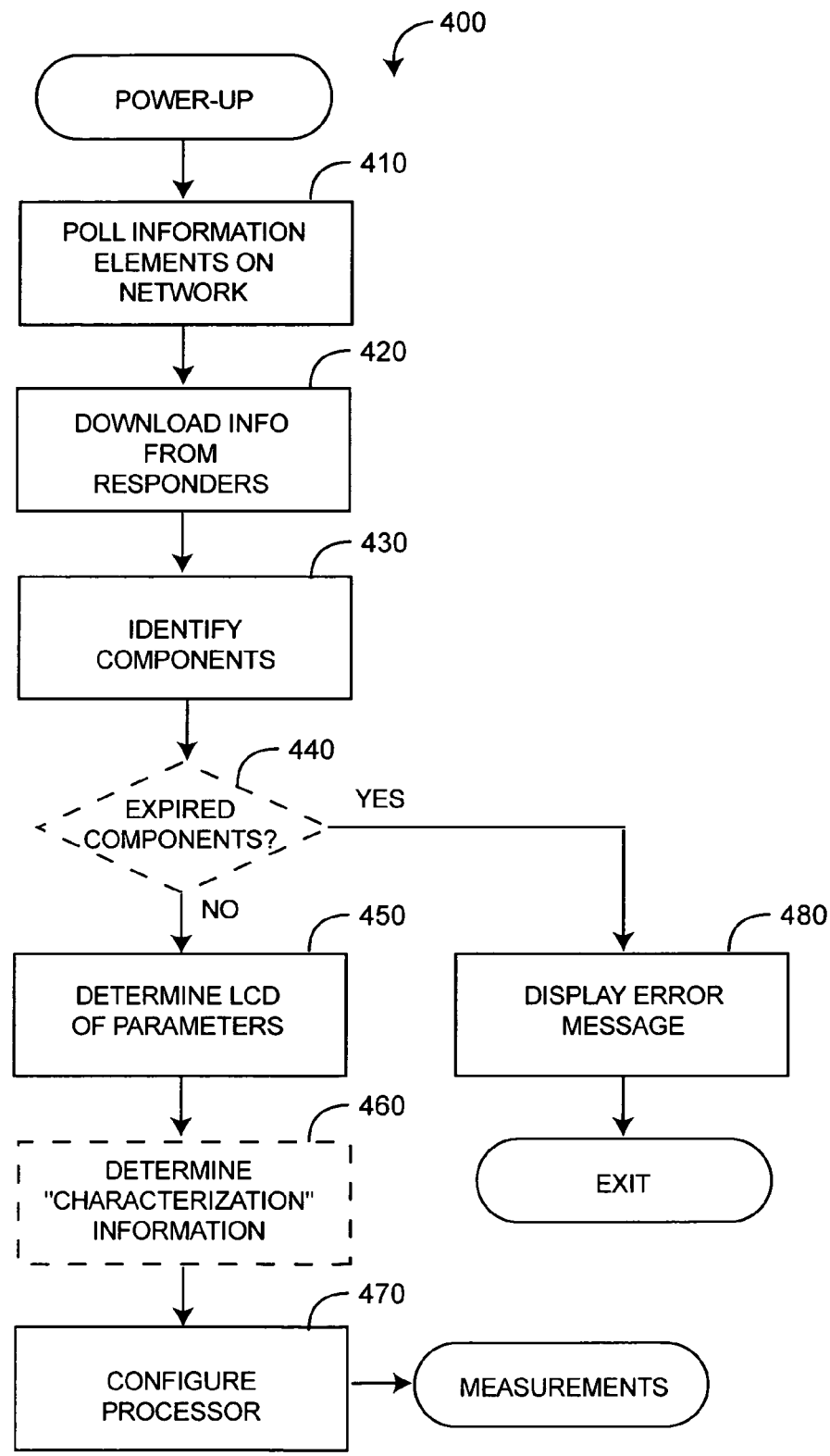
FIG. 4 is a flowchart of a physiological measurement system configuration process.

FIG. 4 illustrates a configuration process 400 for a physiological measurement system 200 (FIG. 2). This process is executed by the network controller 301 (FIG. 3) or the processor 210 (FIG. 2) or both with respect to information elements 314-334 (FIG. 3) that exist on the network 305 (FIG.

3). After system power-up, any information elements on the network are polled 410 so they identify themselves. Information is then downloaded from the responding information elements 420. In one embodiment, download information can be some or all of Identification (ID), Life, Parameters, Characterization and Features information. ID identifies a component on the network, either the type of component generally, such as a sensor or cable, or a particular part number, model and serial number, to name a few. As another example, ID for a disposable sensor portion 224 (FIG. 2) may be an attachment location on a patient and ID for a reusable sensor portion 222 (FIG. 2) may be a patient type.

Life, for example, may be a predetermined counter written into an EEPROM to indicate the number of uses or the length of use of a particular component. Then, Life is counted down, say each time power is applied, until a zero value is reached, indicating component expiration.

Parameters specifies the measurements the component is capable of supporting, which may include, for example, one or more of $SpO_2$, HbCO, MetHb, fractional $SpO_2$, Hbt, NIBP and blood glucose to name just a few. With respect to a sensor, Parameters depend on the number of emitters, emitter wavelength and emitter configuration, for example. For a cable, Parameters depend on the number of conductors and connector pinouts, for example. Parameters may also simply reflect a license to use a component, such as disposable tape, with respect to a particular system configuration.

Features set the mode for the processor or other system elements. As one example, Features specify the mode or modes of one or more algorithms, such as averaging.

Characterization allows the processor to "plug and play" with a particular component. For example, if the component is a sensor, Characterization may include information necessary to drive the emitters, such as the LED wavelengths and drive pattern. Characterization may also include calibration data for the parameters measured. As another example, Characterization for a sensor component 220 (FIG. 2) may indicate sensitivity to a probe-off condition depending on the sensor type. Probe-off detection is described in U.S. Pat. No. 6,654,624 entitled Pulse Oximeter Probe-Off Detector and U.S. Pat. No. 6,771,994 entitled Pulse Oximeter Probe-Off Detection System, both assigned to Masimo Corporation and incorporated by reference herein.

As shown in FIG. 4, components are identified 430 from downloaded ID information. If any of the information elements provide Life information, a check is made to determine if the corresponding component is expired 440. If so, an error message is displayed 480. The message may be a warning to replace the component or it may indicate that the system is nonfunctional. Next, the least common denominator (LCD) of the parameters is determined 450 from the Parameters information. This is described in further detail with respect to FIGS. 5A-B. Characterization is determined 460, if necessary for a particular component, such as a daughterboard or sensor. Finally, the processor is configured 470 and the system is ready to begin parameter measurements.

Figure 5A:
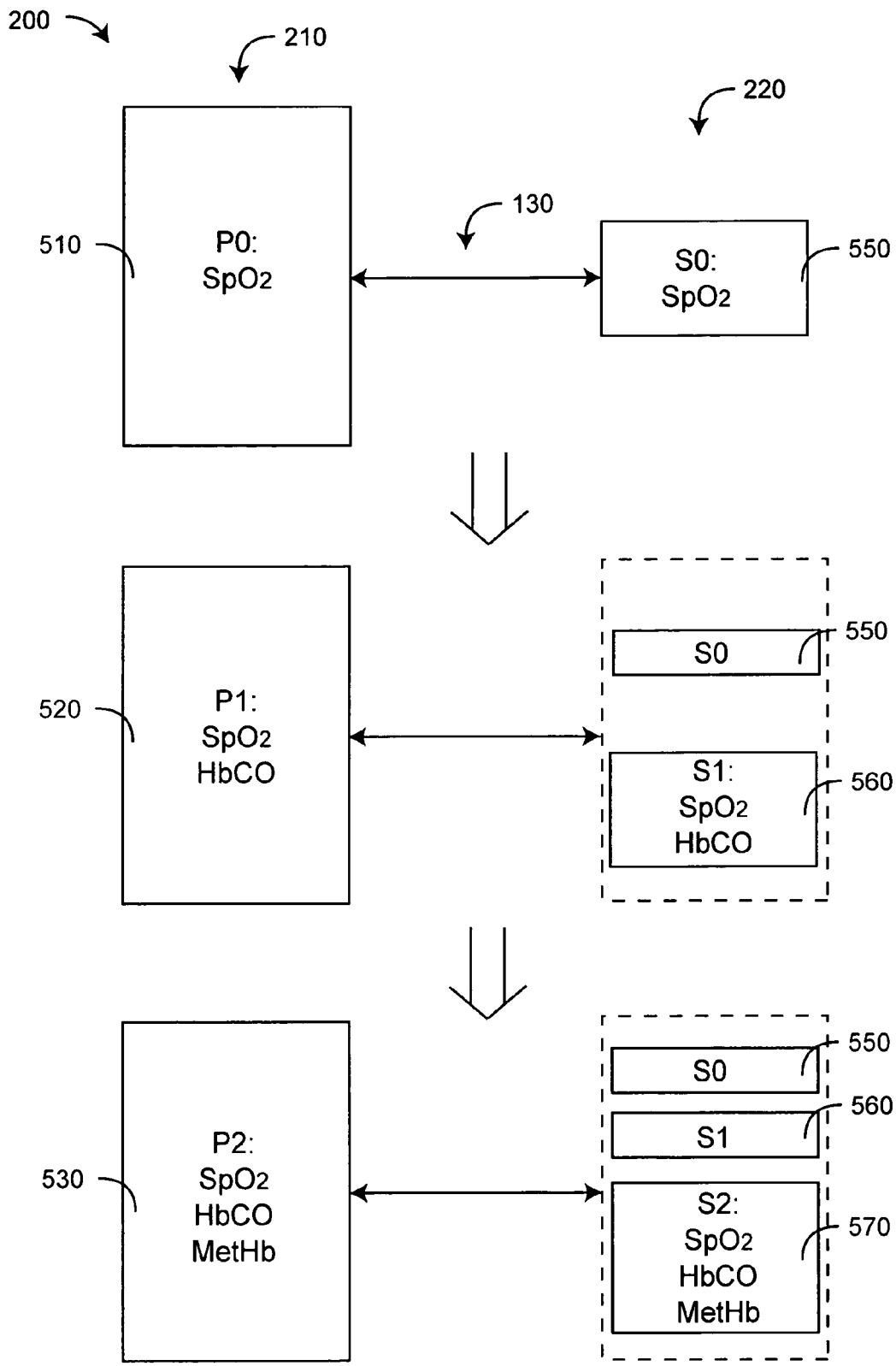
FIGS. 5A-B are block diagrams illustrating forward and backward sensor compatibility with various processors.
Figure 5B:
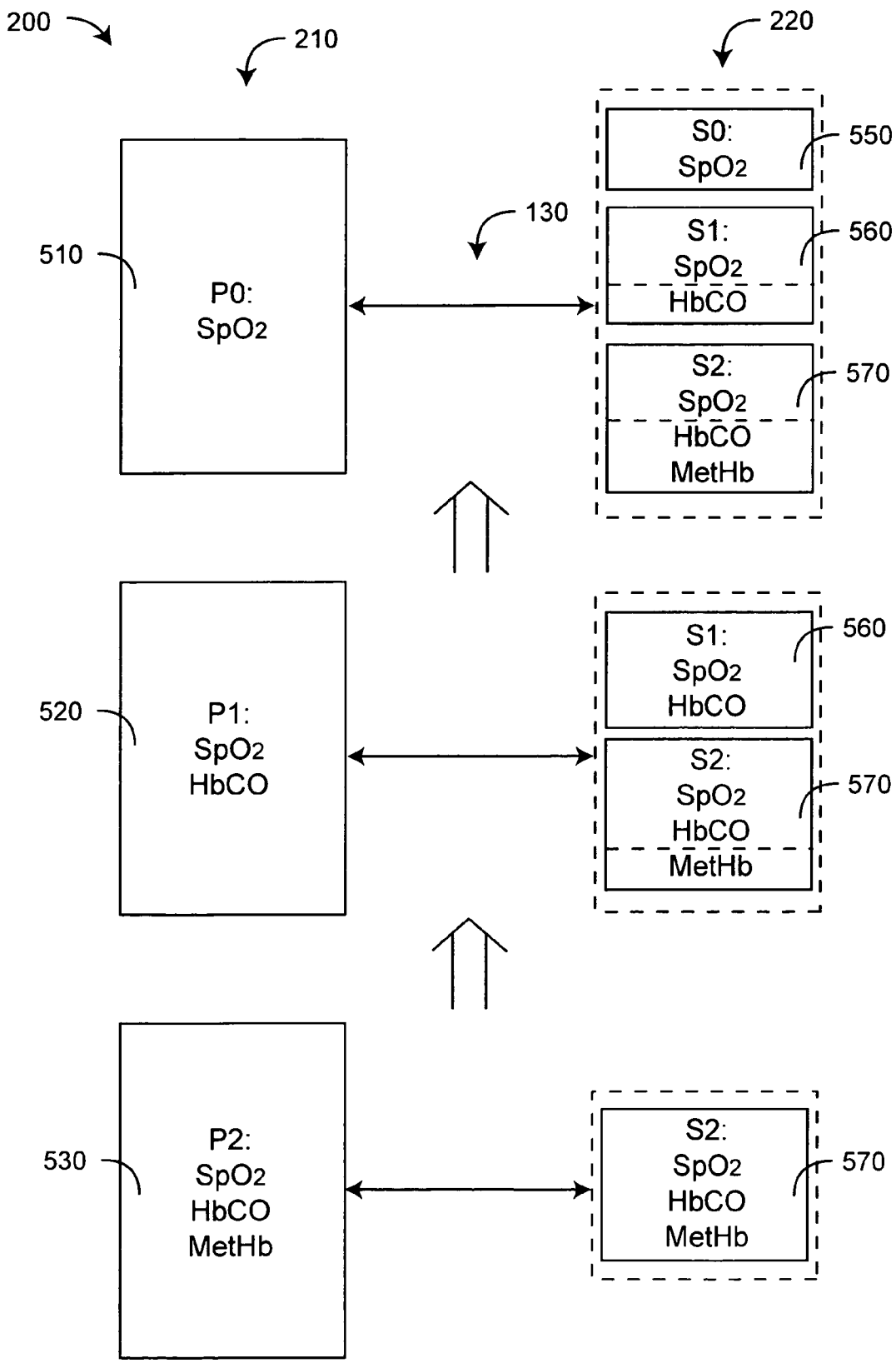

FIGS. 5A-B illustrate embodiments of a configurable physiological measurement system 100 demonstrating both forward sensor compatibility (FIG. 5A), and backward sensor compatibility (FIG. 5B). Further, the parameter measurement capability of each system 100 is determined by the least common denominator (LCD) of the parameter capabilities of a processor 210 and a sensor 220.

As shown in FIG. 5A, configurable physiological measurement systems 200 comprise a family of processors (P0, P1, P2) 210 including those capable of computing $SpO_2$ 510-530, HbCO 520-530 and MetHb 530. The systems 200 also comprise a family of sensors 220 (S0, S1, S2) including those capable of detecting $SpO_2$ 550-570, HbCO 560-570 and MetHb 570. Here, the lower numbered processors and sensors represent less capability, e.g. older generation processors and sensors or current generation, but less costly processors and sensors. Illustrated is forward sensor compatibility, i.e. less capable sensors are capable of running on more capable processors. For example, an $SpO_2$ only sensor 550 is capable of working with a multiple parameter ($SoO_2$, HbCO, MetHb) processor 530. Also illustrated is LCD functionality. A system 200 having a P2 processor 530 and a S0 sensor 550 is functional but only capable of measuring $SpO_2$.

FIG. 5B illustrates backward sensor compatibility, i.e. more capable sensors are capable of running on less capable processors. For example, a multiple parameter ($SpO_2$, HbCO, MetHb) sensor 570 is capable of working with an $SpO_2$ only processor 510. Also, a system 200 having a P0 processor 510 and a S2 sensor 570 is functional, but only capable of measuring $SpO_2$.

Forward and backward sensor compatibility is described above with respect to configurable physiological measurement systems 200 having various processor 210 capabilities and sensor 220 capabilities. The configurable physiological measurement systems 200 can have any or all of the processor 210, sensor 220 and cable 230 components described with respect to FIG. 2, above. As such forward and backward compatibility is equally applicable to combinations of processor 210 and cable 230 or combinations of sensor 220 and cable 230, including the components of such described with respect to FIG. 2, where the capability of such combinations is determined by LCD functionality, as described above.

A configurable physiological measurement system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological measurement system comprising:
    a sensor configured to transmit light having a plurality of wavelengths into a tissue site and to generate a sensor signal responsive to the transmitted light after tissue attenuation;
    a processor configured to operate on the sensor signal so as to derive at least one physiological parameter;
    a communications link adapted to provide communications between the sensor and the processor; and
    a plurality of information elements distributed across at least one of the sensor, the processor and the communications link,
    wherein the information elements provide operational information corresponding to at least one of the sensor, the processor and the communications link, the processor configured to determine a least common denominator of parameter measurement capabilities based on the operational information.

2. The physiological measurement system according to claim 1 further comprising a network controller capable of reading the information elements and providing the information to the processor.

3. The physiological measurement system according to claim 1 wherein the sensor comprises a reusable portion and a disposable portion, each having at least one of the information elements.

4. The physiological measurement system according to claim 3 further comprising:
    attachment data provided by a first information element associated with the disposable portion describing where the sensor is attached; and patient data provided by a second information element associated with the reusable portion describing patient type.

5. The physiological measurement system according to claim 1 further comprising:
at least one sensor information element associated with the sensor; and
sensor type data readable from the sensor information element,
wherein the processor utilizes the sensor type data to determine a sensitivity to a probe-off condition where the sensor is not properly positioned with respect to the tissue site.

6. A physiological measurement system comprising:
a sensor configured to transmit light having a plurality of wavelengths into a tissue site and to generate a sensor signal responsive to the transmitted light after tissue attenuation;
a processor configured to operate on the sensor signal so as to derive at least one physiological parameter;
a communications link adapted to provide communications between the sensor and the processor; and
a plurality of information elements distributed across at least one of the sensor, the processor and the communications link,
wherein the information elements provide operational information corresponding to at least one of the sensor, the processor and the communications link and wherein the processor comprises a processor board and a daughter board, each having at least one of the information elements.

7. The physiological measurement system according to claim 6 wherein the communications link is a cable having a patient cable portion and a sensor cable portion, each portion having at least one of the information elements.

8. In a physiological measurement system, a sensor configured to transmit light having a plurality of wavelengths into a tissue site and to generate a sensor signal responsive to the transmitted light after tissue attenuation, a processor configured to operate on the sensor signal so as to derive at least one physiological parameter and a communications link adapted to provide communications between the sensor and the processor, the sensor comprising:
a disposable portion of the sensor having a first information element; and
a reusable portion of the sensor having a second information element,
wherein the disposable portion is capable of removable attachment to the reusable portion, and
wherein the first information element and the second information are readable by the processor so as to determine the operational capability of the sensor and wherein the processor is configured to determine a least common denominator of parameter measurement capabilities.

9. The sensor according to claim 8 further comprising parameter information associated with at least one of the first information element and the second information element indicating physiological parameter measurements supported by at least one of the disposable portion, the reusable portion and the combination of the disposable portion and the reusable portion.

10. The sensor according to claim 9 wherein the parameter information comprises information relating to characteristics of light emitters incorporated on at least one of the disposable portion and the reusable portion.

11. The sensor according to claim 8 further comprising:
attachment information associated with the first information element describing where on a patient the sensor is attached; and
patient information associated with the second information element describing a patient type.

12. The sensor according to claim 8 further comprising sensor life information associated with the first information element that is updated according to a sensor usage measure.

13. The sensor according to claim 8 further comprising characterization information associated with at least one of the first information element and the second information element indicating at least one of light emitter wavelengths, light emitter drive requirements and calibration data.

14. A physiological measurement method for a system having a sensor configured to transmit light having a plurality of wavelengths into a tissue site, a processor configured to operate on a sensor signal responsive to the transmitted light after tissue attenuation and a communications link configured to provide communications between the sensor and the processor comprising the steps of:
reading a plurality of information elements distributed among at least one of the sensor, the processor and the communications link;
identifying components of the system based upon data read from the information elements;
determining a physiological parameter that the system is capable of measuring by determining a least common denominator of parameter measurement capabilities of the identified system components; and
configuring the processor to measure the physiological parameter.

15. The physiological measurement method according to claim 14 comprising the further step of characterizing at least one of the system components based upon data read from the information elements.

16. The physiological measurement method according to claim 15 comprising the further step of determining if any of the system components are expired.

17. The physiological measurement method according to claim 16 wherein the reading step comprises the substeps of:
polling memory devices connected to a network; and
downloading information from responding memory devices.

18. A physiological measurement system having sensor, communication and processor components configured to derive at least one physiological parameter based upon light having a plurality of wavelengths transmitted into a tissue site and detected after tissue attenuation, the physiological measurement system comprising an information element network means for allowing various configurations of the components to interoperate without modification, wherein the information element network means provides operational information and the processor component is configured to determine a least common denominator of parameter measurement capabilities based on the operational information.

19. The physiological measurement system according to claim 18 wherein the information element network means comprises a network controller means for reading data from individual information elements of the network.

20. The physiological measurement system according to claim 19 wherein the network controller means comprises a parameter means for determining the parameter measurement capability of the combined system components.

* * * * *

UNITED STATES PATENT AND TRADEMARK OFFICE
CERTIFICATE OF CORRECTION

PATENT NO. : 7,729,733 B2
APPLICATION NO. : 11/367036
DATED : June 1, 2010
INVENTOR(S) : Al-Ali et al.

It is certified that error appears in the above-identified patent and that said Letters Patent is hereby corrected as shown below:

At column 1, line 60 (approx.), change "$\varepsilon_{i,\lambda}$," to --$\varepsilon_{i,\lambda}$--.

At column 2, line 1, change "$\mu_{\alpha,\lambda}$," to --$\mu_{a,\lambda}$--.

At column 6, line 7, change "$SoO_2$," to --$SpO_2$,--.

Signed and Sealed this
Twenty-eighth Day of December, 2010

David J. Kappos
*Director of the United States Patent and Trademark Office*